:::
United States Patent [19]

Brunnett

[11] 4,052,620

[45] Oct. 4, 1977

[54] METHOD AND APPARATUS FOR IMPROVED RADIATION DETECTION IN RADIATION SCANNING SYSTEMS

[75] Inventor: Carl J. Brunnett, Mayfield Heights, Ohio

[73] Assignee: Picker Corporation, Cleveland, Ohio

[21] Appl. No.: 636,212

[22] Filed: Nov. 28, 1975

[51] Int. Cl.$^2$ ............................................. G01N 23/08
[52] U.S. Cl. ............................. 250/445 T; 250/416 R
[58] Field of Search ............... 250/445 T, 402, 416 R; 328/63

[56] References Cited

U.S. PATENT DOCUMENTS

| 2,745,019 | 5/1956 | Hamacher | 250/416 R |
|---|---|---|---|
| 3,573,461 | 4/1971 | Ohlsson | 250/402 |
| 3,714,429 | 1/1973 | McAfee et al. | 250/445 T |
| 3,778,614 | 12/1973 | Hounsfield | 250/445 T |

*Primary Examiner*—Craig E. Church
*Assistant Examiner*—B. C. Anderson
*Attorney, Agent, or Firm*—Watts, Hoffmann, Fisher & Heinke Co.

[57] ABSTRACT

An improved radiation measuring and processing unit for a radiation scanning system precisely determines the average intensity of a beam of radiation as it impinges upon a radiation detector during a primary time period of predetermined duration. The unit computes the average intensity by detecting the average rate of a train of intensity representing pulses occurring during a secondary time period whose duration is determined according to the occurrences of the pulses within the primary time period. The system is preferably a transverse section, X-ray scanning system, and the radiation detector generates a data signal having a level indicative of the intensity of the beam of X-radiation after it passes through a subject. The measuring and processing unit includes a pulse generator, preferably in the form of a charge pump integrator, for converting the data signals into the train of data pulses having a repetition rate which varies according to the level of the data signal. The unit also includes a data counter and a time counter which are operative throughout a series of the primary time periods. The time counter counts a series of clock pulses indicative of the lapse of time between the first and last data pulses occurring during the primary time period, thereby establishing the secondary time period. The data counter counts all pulses occurring during the secondary time period, i.e., the second and subsequent data pulses occurring during the primary time period. Comparison of the contents of the data and time counters at the end of the primary time period provides an accurate indication of the average intensity of the X-ray beam as it impinges upon the detector.

18 Claims, 19 Drawing Figures

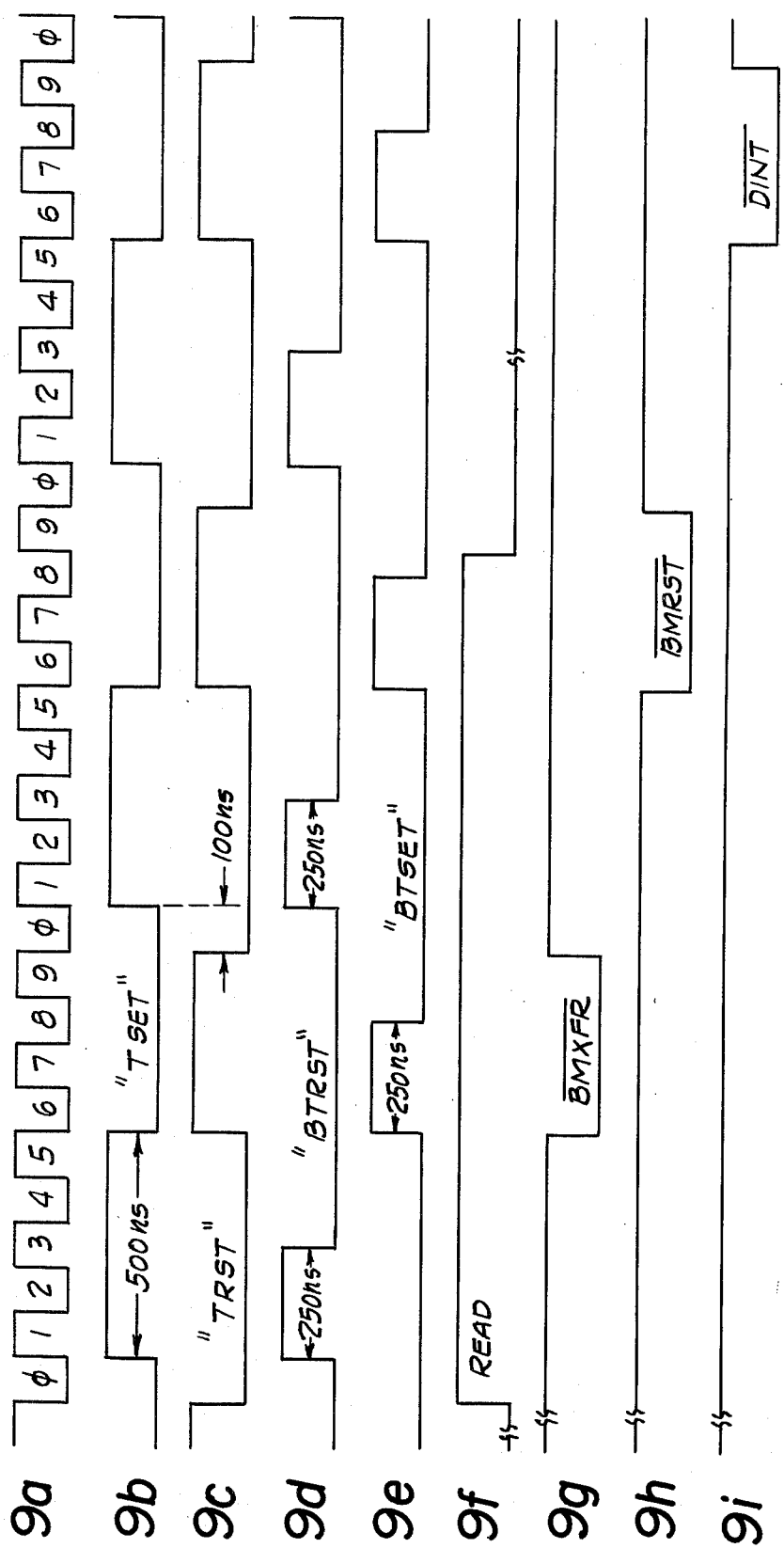
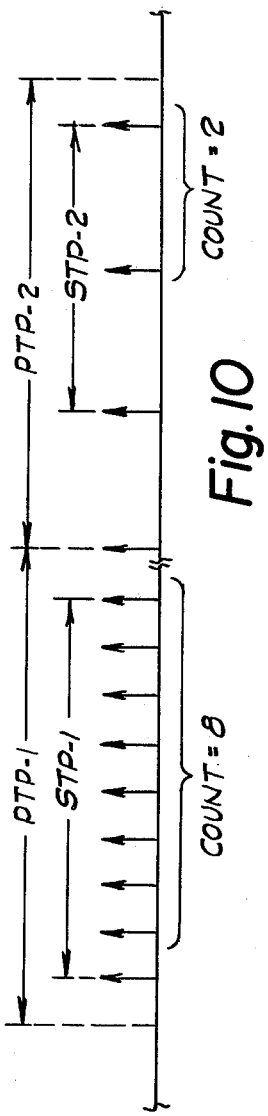
Fig. 9
Fig. 10

METHOD AND APPARATUS FOR IMPROVED RADIATION DETECTION IN RADIATION SCANNING SYSTEMS

REFERENCES TO RELATED AND RELEVANT PATENT APPLICATIONS

United States patent application Ser. No. 559, 411, filed Mar. 18, 1975, entitled TOMOGRAPHY SYSTEM HAVING NON-CONCURRENT COMPOUND AXIAL SCANNING (the SINGLE MOTION patent application);

United States patent application Ser. No. 559,412, filed Mar. 18, 1975, entitled TOMOGRAPHY SYSTEM HAVING AXIAL SCANNING (the DUAL MOTION patent application);

United States patent application Ser. No. 635,952 filed Nov. 28, 1975, entitled TRANSVERSE TOMOGRAPHY SYSTEM HAVING MULTIBEAM ORBITAL SCANNING WITH ALL BEAMS OFFSET FROM THE CENTER OF ORBIT (the BACKSIDE SCANNING patent application).

BACKGROUND OF THE INVENTION

This invention relates generally to systems for nondestructively examining objects using penetrative radiation and, more particularly, relates to an improved method and apparatus for measuring the intensity of X-radiation emerging from the subject of a clinical examination.

FIELD OF THE INVENTION

A conventional radiograph is a two-dimensional shadow image of a three-dimensional subject. The depth dimension is not apparent since all interior structures of the subject appear to be in a single plane. As a consequence, in some circumstances a conventional radiograph may fail to provide necessary detail concerning relative spatial locations of interior structures, is difficult to interpret, and may not reveal the existence of a condition of interest in the subject.

Tomographic procedures have been developed to fulfill some objectives which are unobtainable by conventional radiographical procedures. In tomography, an image viewed from a cross-sectional plane of interest extending through a subject is developed by sequentially directing X-rays through the subject from a plurality of directions. The resulting image reveals relative spatial relationships of internal structures of the subject in the plane of interest.

Early tomographic systems utilized a radiation detector whose movement was coordinated with movement of a radiation source which directed a radiation beam to the detector. The source-detector pair moved about an axis passing through the subject, and the system produced a cross-sectional image of the subject substantially in a selected plane of interest which extended transverse to the axis of the X-ray beam. The source-detector motion of this scanning technique resulted in substantially continuous changes in the spatial relationship between the detector and the source and the internal structure of the subject. These changes blurred images of the structures out of the plane of interest with the result that an image of the structures in the plane of interest was produced.

Other tomographic procedures have been proposed which develop a cross-sectional image of the subject viewed from a plane which includes the axis of the X-ray beam. Tomography which produces such images is known as transverse section tomography. This type of tomography has resulted in production of a reconstructed image, or representation, of a transverse section through the subject being examined.

Transverse section scanning has evolved into two general types of systems. In one such system a radiation source-detector pair is translated linearly while scanning the subject with a radiation beam having its axis lying in a plane containing the section of the subject to be examined. A number of such scans or linear translations are completed during each examination with the angular orientation of the beam relative to the subject being changed from one scan to another. Each scan is divided into individual scan segments. The radiation passing through the subject during each scan segment constitutes, in effect, a single beam passing through the subject along a narrow path. The detected intensity of the beam for each scan segment is recorded for computing X-ray transmission (or X-ray absorption) characteristics of the subject. The characteristics are appropriately processed to provide a reconstructed image of the internal structure of the subject in the scanned plane.

In a proposed transverse section scanning system, a radiation source-detector pair orbits about the subject while producing a beam having its axis lying in a plane. After each orbit the source-detector pair is incrementally pivoted about an axis normal to the plane of interest and passing through the source, and another orbit in the same plane is completed. Each orbital scan is formed by a continuous succession of individual scan segments, and the intensity of the beam for each scan segment is detected and recorded for computing the X-ray transmission or absorption characteristics of the subject. The data accumulated from the scans are processed to produce a reconstructed image viewed from the plane.

In a modification of the noted "orbital" system, multiple closely spaced detectors have been used with a common X-ray source. Use of multiple detectors enables, in some circumstances, production of good image resolution after a single orbit of the source and detectors about the subject. In effect the single detector-multiple scan approach is traded off, at least in some circumstances, for a multiple detector-single scan approach. These approachs are described in the DUAL MOTION, the SINGLE MOTION, and the BACKSIDE SCANNING applications.

Transverse section tomography systems of both general types have commonly utilized a computational technique known as "back projection" for processing the radiation intensity data to reconstruct the image. The detected intensity of the X-ray beam passing through the subject along a given narrow path (defined by a scan segment) is back projected, or attributed, to all points in a reconstruction matrix which correspond to the path of the beam. The values of radiation transmission intensity measured for all such paths during all the scans are back projected in the matrix to produce a scan-by-scan build-up, or reconstruction, of the image.

More specifically, each value of the radiation transmission as it is back projected in the matrix for a given path is kept constant, and the respective values of each back projection at points of intersection of the respective paths are combined. Each point on the reconstructed image is therefore representative of the sum of the back projected intensities of the paths passing through that point. This technique is described in Kuhl, "A Clinical Radioisotope Scanner for Cylindrical and Section Scanning," PROC. SYMP., Athens 1964, Medical Radioisotope Scanning, I.A.E.A., Vienna, 1, 273, 1964.

The back projection technique has been improved with the introduction of filtered back projections and data processing using Fourier analysis. A discussion of Fourier reconstruction using filtered back projections is set forth in Chesler, "Positron Tomography and Three Dimensional Technique," PROC. SYMP. on Radionuclei Tomography, New York, N.Y., 1972. An algorithm for processing the data using convolutions on a digital computer is given in Shepp, et al., "Some Insights into the Fourier Reconstruction of a Head Section," Bell Laboratories, Murray Hill, N.J., 1974.

PRIOR ART

Fundamental to the success of the tomograhic scanning systems utilizing reconstruction tomography procedures is the ability to accurately determine the intensity of an X-ray beam as it impinges upon a detector after having emerged from the subject. In these scanning systems the detector includes a scintillator coupled with a photomultiplier tube for generating an analog data signal whose level is representative of the intensity of the detected radiation.

The fundamental approach to measuring the intensity of the detected radiation has been to integrate the data signal over the time period of the scan segment, called an integration interval, to produce a signal representative of the average detected intensity over that time period. Early proposals for doing this employed a conventional integrator for integrating the data signal throughout the integration interval and an analog-to-digital converter for converting the integrated data signal to a digital value. This digital value, when compared with the duration of the time period, represented the average detected intensity of the beam over the period.

Because the integrated data signal was an analog signal, evaluating it with extreme precision was difficult. Accordingly the statistical accuracy of the radiation intensity measurements produced by this approach was limited. The integrators themselves introduced an unavoidable delay in processing the data signals with the extent of the delay being proportional to the bandwidth of the integrator. When wide bandwidth integrators were employed for accommodating a wide range of data signal values, the processing delay produced by the integrators tended to be maximized. The delays were inherent in the construction of the integrators and to the extent the delays were not completely compensated for, the statistical accuracy of the radiation intensity measurements suffered.

A subsequent approach which improved statistical accuracy somewhat used a data signal amplitude-to-frequency converter. In one prior art system the data, signal was converted to a variable frequency signal ranging from zero to ten megahertz in direct proportion to the data signal amplitude. In this approach, a conventional integrator circuit was coupled with a threshold detector. The integrator was operated so that its output level was driven below the threshold of the threshold detector immediately after the integrator output level exceeded the threshold. This caused the threshold detector to produce a train of data representing pulses whose frequency varied in direct relation to variations in the data signal level.

The variable frequency data pulse approach improved statistical accuracy since the number of pulses occurring during a given integration interval could be accurately counted. An average frequency was determined by, in effect, dividing the pulse count by the duration of the integration interval, and the resulting value represented the average detected radiation intensity for the corresponding path traversed by the X-rays. The bandwidth related processing delay inherent in the construction of the integrator adversely affected the operation of these systems because, during the time the integrator output was driven below the threshold level of the threshold detector, the integrator circuit was disabled from responding to input data signals. As a result, input data was irretrievably lost. Minimizing the loss of data in these systems required elaborate high speed, relatively expensive electronics if acceptable operation at high frequencies (e.g., up to 10 megahertz) were to be expected.

An improved voltage-to-frequency converter utilizing a different integrator circuit, known as a charge pump integrator, was recently developed. Charge pump integrators include a charge generator associated with an integrator circuit. The charge generator selectively dispenses charge to the integrator circuit each time the integrator output level exceeds a threshold. This coaction allows substantially all input current to be utilized by the integrator while providing a low delay, wide bandwidth circuit.

One such voltage-to-frequency converter is commercially available from Teledyne Filbrick Corporation under Model No. 4707, and is described by that company's data sheet of Oct. 15, 1974. One suggested application for this converter is in nuclear data acquisition wherein the input current may vary between 0 and 850 microamps. While such input current levels are acceptable for nuclear data acquisition, tomographic X-ray systems typically generate 10 microamps maximum input current, therefore rendering the referenced voltage-to-frequency converter unsuitable for X-ray tomographic applications.

Another limitation encountered with the variable frequency data pulse approach was that, if the data pulse frequency is low compared to the extent of the integration interval, errors of substantial magnitude could be encountered in determining the average frequency for any given integration interval. More specifically, the integration interval may begin and end at any point between the occurrences of sequential data pulses. Assuming for the purposes of discussion, that the data pulse frequency is constant over a period somewhat longer than an integration interval, if the integration interval commences immediately after the conclusion of one pulse and concludes immediately before a pulse, it is apparent that the number of intervening pulses counted during the interval is one less than the count would be if the interval had happened to commence just prior to the first mentioned pulse and included the last mentioned pulse. Accordingly, the pulse count for a given integration interval count differ by a count of one pulse depending upon the occurrence of data pulses, in time, relative to the beginning and end of the integration interval. When the data pulse frequency is high relative to the duration of the integration interval a one-pulse error may be substantially negligible (e.g., of the order of 0.1% where the pulse frequency is 1000 Hertz per integration interval). However, at a low count rate, for example 20 pulses per integration interval, a one-pulse error causes the precision of the measurement to deteriorate to a 5% error.

Still another limitation on the statistical accuracy of the systems referred to resides in variations in extent of the integration interval. Assuming that a constant radiation level is incident on a detector, a constant data signal level is therefore input to the voltage-to-frequency converter. As a result, a constant frequency signal is output from the converter. However, if the integration intervals indicated to the converter are not of precisely equal length, the resultant digital representation of the average detected radiation level will vary from one integration interval to another in accordance with variations in the indicated integration interval.

The extent of the integration intervals in one tomographic scanning proposal has been determined by detecting incremental changes in position of a source-detector pair relative to a fixed reference point. The position detection scheme has utilized a series of equally spaced marks which are scanned by a photosensitive device as the source-detector pair moves. The output from the photosensitive device is a series of pulses, each pulse corresponding in time to a mark disposed at a predetermined location relative to the photosensitive device. The occurrence of each pulse terminates one integration interval and initiates a succeeding interval.

The integration intervals must be of brief duration (e.g., no more than about 5 milliseconds) to obtain acceptable resolution of the tomographic image. This has normally required the marks to be very accurately located, but avoidable variations in relative distance between marks have resulted in inconsistent integration intervals and consequent loss of accuracy.

The foregoing examples assumes that the source-detector pair speed is constant. It should be apparent through, that if the rate of speed of the source-detector pair varies even slightly, the extent of the integration interval is altered with the same resulting effect on system accuracy as that caused by inconsistent mark spacing.

SUMMARY OF THE INVENTION

The present invention provides a new and improved method and apparatus for computing the average detected intensity of a beam of radiation during a predetermined interval wherein the detected beam intensity is represented by a pulsating signal whose frequency varies according to the detected intensity and wherein the accuracy of the computed average intensity of the detected radiation is unaffected by beginning and end points of the interval in time relative to the variable frequency signal pulsations.

The invention is particularly applicable to a transverse section tomographic radiation system including a radiation scanning system for accomplishing a succession of scans of a subject being studied; a data processing unit for processing signals from the scanning unit which are indicative of (1) detected radiation intensity, (2) scan segment intervals, and (3) radiation path location relative to the subject; and an imager which receives reconstructed image signals output from the data processing unit and produces a cross-sectional image of a desired planar section of the subject.

The cross-sectional image of the subject is reconstructed by use of detected radiation intensity data accumulated from small segments of a number of scans of the radiation in the plane of the cross-section of the subject. In a preferred embodiment of the invention each of the scan segments is defined in time by a primary time period during which the detected radiation passes through the subject along a narrow path in the plane (i.e., the radiation is effectively a narrow beam).

Radiation intensity detected during each primary time period is represented by an analog DATA signal which is converted to a pulsating signal whose frequency varies as a function of the amplitude of the DATA signal. Pulsations of the converted DATA signal occurring during the primary time period are counted and the occurrence of the pulsations is used to define a secondary time period of variable duration within the primary time period. The pulse count for a given secondary period is compared to the actual extent of the secondary period to provide a relatively precise indication of the average radiation intensity detected during the secondary period.

This average intensity is attributed to the entire primary time period, and thus to the beam path of the corresponding scan segment, in reconstructing an image of the subject. As a result, statistical error resulting from small unavoidable variations in the extent of the primary time periods from scan segment to scan segment are obviated. Moreover, statistical errors which could be encountered as a result of variations in relative positions (in time) of the beginning and end of the primary time period with respect to the occurrence of the converted DATA signal pulsations are avoided.

In the preferred embodiment of the invention, an X-ray tomographic scanning system having an X-ray source and an associated X-ray detector is employed. The detector produces analog DATA signals representative of the detected intensity of X-rays which have passed through a subject under study. The scanning system is constructed and arranged to produce a sequence of READ signals which signal the end of each primary time period and the beginning of the next succeeding period. The scanning system also produces POSITION signals which serve to identify, relative to the subject, the path traversed by the X-rays during each scan segment.

The data processing unit processes the DATA, READ and POSITION signals to produce an AVERAGE INTENSITY signal representing the average detected X-ray intensity for each X-ray path through the subject. The AVERAGE INTENSITY signals are, in turn, processed and combined by the data processing unit to produce RECONSTRUCTED IMAGE signals which are output to the imager. The data processing unit includes a data signal processor and a reconstruction processor. The data signal processor receives READ and DATA signals from the scanning system and produces a first output signal representative of the extent of a secondary time period (occurring within the primary time period) during which X-rays are indicated as being detected, and a second output signal representative of an amount of radiation detected in one path during the secondary time period. The reconstruction processor combines these signals to produce the AVERAGE INTENSITY signal which represents the average radiation intensity detected in the path throughout the primary time period.

The data signal processor preferably converts the analog DATA signals to variable frequency pulsating signals. The data signal processor also initiates the secondary time period coincident with the first data pulse occurring within the primary time period, and terminates the secondary time period coincident with the last pulse occurring within the primary time period. Accordingly, the extent of the secondary time period, during which the pulses actually occur, is precisely determinable and is accurately represented by the first output signal. Pulses occurring during the secondary time period are counted by the data signal processor and the number of pulses counted is accurately represented by the second output signal.

The reconstruction processor, in a preferred embodiment of the invention, includes a comparator which compares the first and second data signal processor output signals and produce the AVERAGE INTENSITY signal. The reconstruction processor also receives POSITION signals output from the scanning system so that each AVERAGE INTENSITY signal can be correlated with the position of its respective path relative to the subject.

The reconstruction processor accumulates the data represented by the AVERAGE INTENSITY signals and processes the data to, in effect, reconstruct an image from the data and produce the RECONSTRUCTED IMAGE signal for operating the imager.

Another feature of the invention resides in the use of, in an X-ray tomographic system, a charge pump integrator designed for accommodating analog DATA signals output from an X-ray detector and converting the DATA signals to a variable frequency pulsating signal without incurring appreciable loss of signal information.

The charge pump integrator includes an integrator circuit, a threshold level detector, an output circuit, and a feedback circuit. The integrator circuit responds to the DATA signal and tends to produce an integrated data signal characteristic of the integral of the DATA signal. The threshold level detector is coupled to the output of the integrator and produces a threshold detector output whenever the integrator output signal exceeds the threshold of the threshold level detector. The threshold detector output is received by the output circuit which is coupled to the integrator input via the feedback circuit. Whenever a threshold detector output is produced the feedback circuit momentarily and abruptly causes the integrator output signal to drop below the threshold level of the threshold detector. Accordingly, the threshold detector output is abruptly cut off and the output waveforms of both the integrator circuit and the threshold detector are variable frequency pulse trains. The feedback circuit preferably operates by discharging a feedback capacitor associated with the integrator circuitry by a predetermined quantum each time a threshold detector output is detected. This is accomplished quite rapidly so that the integrator circuit remains substantially continuously responsive to the DATA signal input to it.

A general object of the present invention is the provision of a new and improved method and apparatus for processing data in a tomographic scanning system.

Other objects and a fuller understanding of the invention will be apparent by referring to the following detailed description of a preferred embodiment in conjunction with the accompanying drawings.

BRIEF DESCRIPTION OF THE DRAWINGS

FIGS. 9a–9i illustrate exemplary timing signals used in the system of FIG. 1; and, FIG. 10 is a schematic diagram illustrating the relationship between primary and secondary time periods as defined according to the invention.

DESCRIPTION OF A PREFERRED EMBODIMENT

Figure 1:
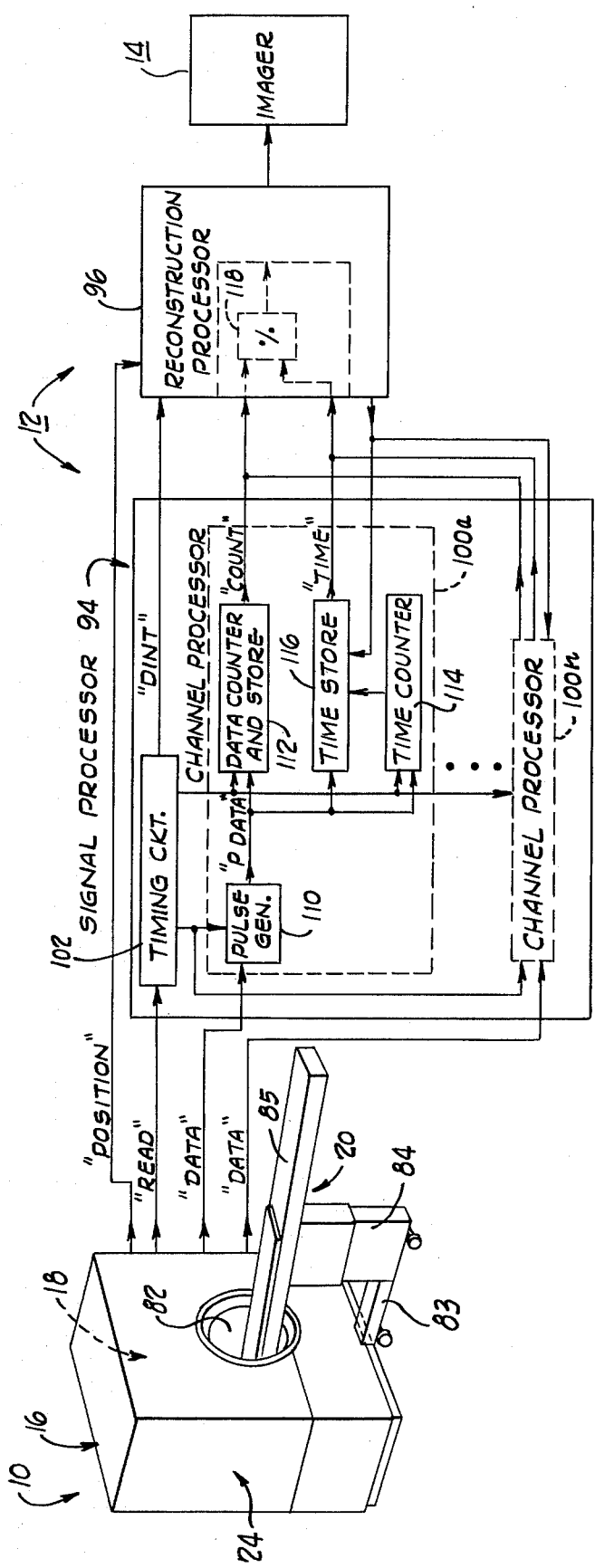
FIG. 1 is a partly perspective, partly schematic drawing of a radiation scanning system employing the invention.
Figures 2, 3, 4:
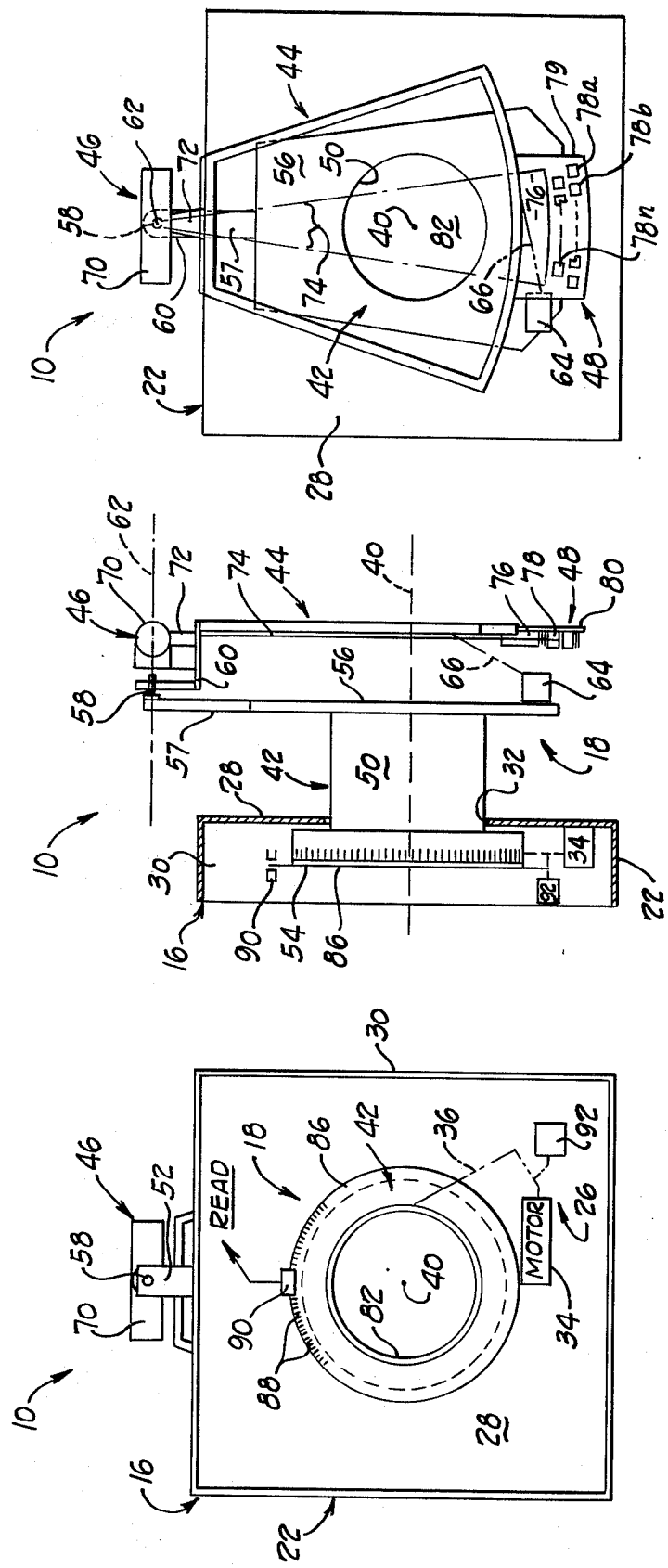
FIGS. 2–4 are views of a scanner used in the scanning system of FIG. 1.

A transverse section X-ray tomography system embodying the present invention is illustrated schematically by FIG. 1. The tomography system includes an X-ray scanning unit 10 for scanning a subject with X-rays in a given plane and producing electrical output information in the form of signals descriptive of the scanning procedure; a processing unit 12 for receiving and processing the scanning unit output signals and producing electrical output signals (RECONSTRUCTED IMAGE signals) representing a transverse cross-sectional view of the subject in the plane; and an imager 14 which responds to the RECONSTRUCTED IMAGE signals to produce an actual image of the transverse cross-sectional view.

The imager 14 can be a display device using a cathode ray tube or an image printing device, either of which can be operated from the processing unit output. Suitable imager devices are already known and therefore the imager 14 is not further illustrated or described in detail.

A scanning system 10 constructed according to a preferred embodiment of the invention is illustrated schematically by FIGS. 1–4 and includes a supporting assembly 16, a scanning assembly 18 movably supported on the assembly 16, and a subject supporting table 20.

The supporting assembly 16 includes a main frame unit 22 (see FIGS. 2–4) which is positioned on a floor of a building in which the system 10 is located, a chassis-like housing assembly 24 (FIG. 1) supported by the main frame for enclosing the assemblies 16, 18, and a drive unit 26 for moving the scanning assembly 18 relative to the supporting assembly 16.

The frame unit 22 includes an upright plate-like rectangular body 28 having a peripheral stiffening flange portion 30 projecting from its circumference transverse to the plane of the body 28. A mounting aperture 32 for the scanning assembly 18 is defined centrally in the body plate 28 and the drive unit 26 is supported on the frame adjacent the aperture 32. The drive unit 26 preferably includes an electric motor 34 drivingly connected to the scanning assembly 18 via an associated drive transmission 36 (schematically illustrated) of suitable construction.

The scanning assembly 18 is connected to the frame 22 for rotation about an axis 40 extending through the aperture 32. The scanning assembly 18 includes a rotatable support unit 42 journaled to the frame 22, a framework 44 movably connected to the support unit 42, and X-ray source and detection assemblies 46, 48, respectively, which are mounted at spaced apart locations on the framework 44. The X-ray source and detection assemblies 46, 48 are rotatable with the support unit 42 and orbit about the axis 40 relative to the frame 22 and are adjustably movable, with the framework 44, relative to the support unit 42.

The support unit 42 includes a tubular cylindrical body 50 extending through the aperture 32 coaxially with the axis 40 and supported on the frame 22 by bearings (not shown) for rotation about the axis 40. A radially outwardly extending flange structure 54 is formed at the end of the body 50 adjacent the frame 22 and the projecting end of the body 50 carries a surrounding flange-like mounting plate 56. The mounting plate 56 includes a projecting arm 57 which carries a trunnion 58 to which the framework 44 is connected.

The framework 44 is preferably constructed from lengths of angle irons which are welded together at their ends to define a generally flat, open frame, and a bearing arm structure 60 extending from the frame to the trunnion 58 so that the framework, along with the supported source and detection assemblies, can pivot about the axis 62 of the trunnion relative to the supporting unit 42. The rotation axis 40 extends through the open center of the framework so that the framework is rotatable about the axis 40 with the unit 42.

A positioning drive motor 64 supported by the plate 56 controls the position of the framework 44 relative to the supporting plate 56 via a suitable transmission schematically illustrated by the reference character 66. The motor and transmission are constructed and arranged so that when the framework is positioned as desired with respect to the axis 62 it is positively locked in the adjusted position.

The X-ray source assembly 46 is schematically illustrating and since it may be of any suitable or conventional construction is not described in detail. As illustrated the X-ray source assembly includes an X-ray tube head 70 defining an X-ray focal spot 71 on the pivot axis 62 and a collimator 72 associated with the tube head for directing X-radiation toward the detection assembly 48 in a fan-shaped beam configuration 74 which is preferably only about two millimeters deep.

The X-ray detection assembly 48 is supported by the framework 44 opposite the source assembly 46 and includes a collimator 76, a plurality of X-ray detector units 78a-78n, and a supporting apron 79 for the collimator and detector units.

The collimator 76 is supported in the path of the X-ray beam 74 and defines a series of narrow slots corresponding in number to the number of detector units 78 so that a narrow pencil beam of X-rays impinges on each detector unit 78. Any reasonable number of detector units can be employed, and twenty such units have been selected for use in one scanning unit.

The detector units may be of any suitable or conventional structure each preferably includes an X-ray excitable scintillation crystal element which is optically coupled to a photomultiplier tube.

The source assembly 46 and the detection assemblies 48 are fixed with respect to each other on the framework 44 so that as the support unit 42 rotates, the source and detection assemblies orbit about the axis 40 while the beam 74 is continuously directed from the source to the detection assemblies 48.

The housing assembly 24 (see FIG. 1) is detachably connected to the frame 22 and extends about the scanning assembly 18 to protect and prevent unauthorized access to internal components of the scanning system.

The component parts of the scanning unit 10 are formed to define a central generally cylindrical opening 82 extending through the scanning unit coaxially with the rotation axis 40. The diameter of the opening 82 is sufficiently large to surround a human torso aligned with the axis 40.

The subject supporting table 20 is schematically illustrated (FIG. 1) as including a wheeled supporting base 83, a pedestal 84, and a subject supporting table top 85 projecting from the pedestal. A supine human subject on the table top 85 is advanced into the opening 82 until a desired section of the subject's body is disposed in the plane of the X-ray beam 74 and with the rotation axis 40 extending through the subject.

The support unit 42 is then rotated about the axis 40 with the X-ray source assembly 46 operated to scan the subject with the beam 74. Since the beam 74 is simultaneously directed to multiple X-ray detector units, a single orbit of the source and detection assemblies about the subject effectively produces a number of scans corresponding to the number of detector units employed in the detection assembly 48. In the reconstructed image resolution provided by a single orbit of the source and detection assemblies about the subject is not sufficient, the framework 44 is pivoted relative to the unit 42 about the trunnion axis 62 and another orbit is completed. This procedure is followed until a desired degree of image resolution can be produced.

During each orbit of the source and detection assemblies the scanning unit produces radiation, index and master index signals which are transmitted to the processing unit 12 to enable eventual reconstruction of an image.

The radiation signals are analog electrical signals which are continuously produced by the photomultiplier tube 81 of each X-ray detector unit and have levels which vary in direct relationship to the intensity of the X-ray beam impinging on the respective detector unit. The DATA signals are individually output from the respective detector units 78a-78n to the processing unit 12.

Each scan of the source and detection assemblies is broken up into a succession of individual scan segments during which X-rays impinging on each detector have traversed a narrow path through the subject. In the preferred embodiment the index signals are a series of pulses, each of which indicates termination of one scan segment and the initiation of the next succeeding scan segment. The index signals are produced by an incremental encoder illustrated in FIGS. 2 and 3 as including an annular timing disc 86 attached to th body flange 54 and bearing a series of substantially equally spaced marks 88 about its periphery and a photosensitive signal producing element 90, such as a photodiode, mounted on the frame 22 adjacent the periphery of the timing disc 86. The markings 88 are accurately located with respect to the disc and each other and are preferably spaced at one-tenth (0.1) degree intervals around the axis 40. Whenever one of the marks 88 moves to a predetermined location relative to the element 90, the element 90 produces a pulse forming an index signal of the pulse train.

The angular velocity of the support unit 42 is maintained substantially constant throughout the period of a complete orbital scan of the subject and accordingly the index signal pulses are of generally uniform frequency, successive pulses occurring at about 0.5-millisecond intervals. This interval between the index signal pulses defines the time period during which the radiation paths for each scan segment are established. The index signals thus provide, in effect, timing signals defining the end and beginning of successive primary time periods during which individual scan segments occur.

The master index signals are produced by a signal generator 92 which is illustrated as associated with the transmission 36. The signal generator 92 produces signals which are uniquely indicative of the angular displacement of the unit 42 from a reference location at any time. The master index signals are thus indicative of the location of the X-ray beam paths relative to the subject at any time.

It should be noted that, in the illustrated embodiment of the invention, the framework positioning motor 64 is controlled from the processing unit 12. As such, the position of the framework 44 relative to the axis 62 is always known and thus the master index signals are effective to accurately locate the X-ray beam paths regardless of position adjustments of the framework 44.

Referring to FIG. 1, the processing unit 12 includes a signal processor 94 for receiving and processing the index and radiation signals from the scanning system 10, and a reconstruction processor 96 coupled to outputs of the signal processor 94 and to the master index signal output from the scanner 10 and effective to produce RECONSTRUCTED IMAGE signals.

The signal processor 94 includes a plurality of channel processor 100a-100n which are each responsive to a respective radiation signal, and a timing circuit 102 which is responsive to the index signals. The timing circuit 102 generates a plurality of timing signals, including TSET, TRSET, BRSET, BTSET, BMXFR, and BMRST, for operating the channel processors 100a-100n to accumulate a number (hereafter the COUNT) corresponding to the intensity received by the associated detector unit in the scanning system 10 during each primary time period.

The channel processing 100a-100n are identically constructed, and are each coupled to the associated detector unit 78a-78n in the scanning system 10. For ease of description, only the channel processor 100a is illustrated and described in detail.

The channel processor 100a includes a pulse generator 110 which is responsive to the radiation signals and to timing signals from the timing circuit 102 for producing a train of pulses, called PDATA pulses, whose rate of occurrence is indicative of the intensity of the radiation impinging upon the associated detector unit. A data counter and store 112 is coupled to the output of the pulse generator 110 and to the timing circuit 102 for counting selected ones of the PDATA pulses occurring during the primary time period and generating a COUNT signal indicative of the number of pulses counted. A time counter 114 is coupled to the pulse generator 110 and to the timing circuit 102 for generating a TIME signal whose value is indicative of the time elapsing between the first and subsequent DATA pulses during the primary time period. A time store 116 is coupled to the pulse generator 110 and to the time counter 114 for storing the value of the TIME signal upon each occurrence of a PDATA pulse subsequent to the first PDATA pulse during the primary time period. Accordingly, at the expiration of the primary time period, the time store 116 contains a value indicative of the duration of a secondary time period beginning with the first PDATA pulse and ending with the last PDATA pulse occurring in the primary time period.

The relationship between primary and secondary time periods is exemplified in FIG. 10 where a pair of primary time periods PTP-1, PTP-2 are illustrated and nine and three PDATA pulses are illustrated and occur within the respective periods. The secondary time periods, STP-1, STP-2 associated with the primary time periods are shown to encompass eight and two PDATA pulses respectively.

Figure 5:
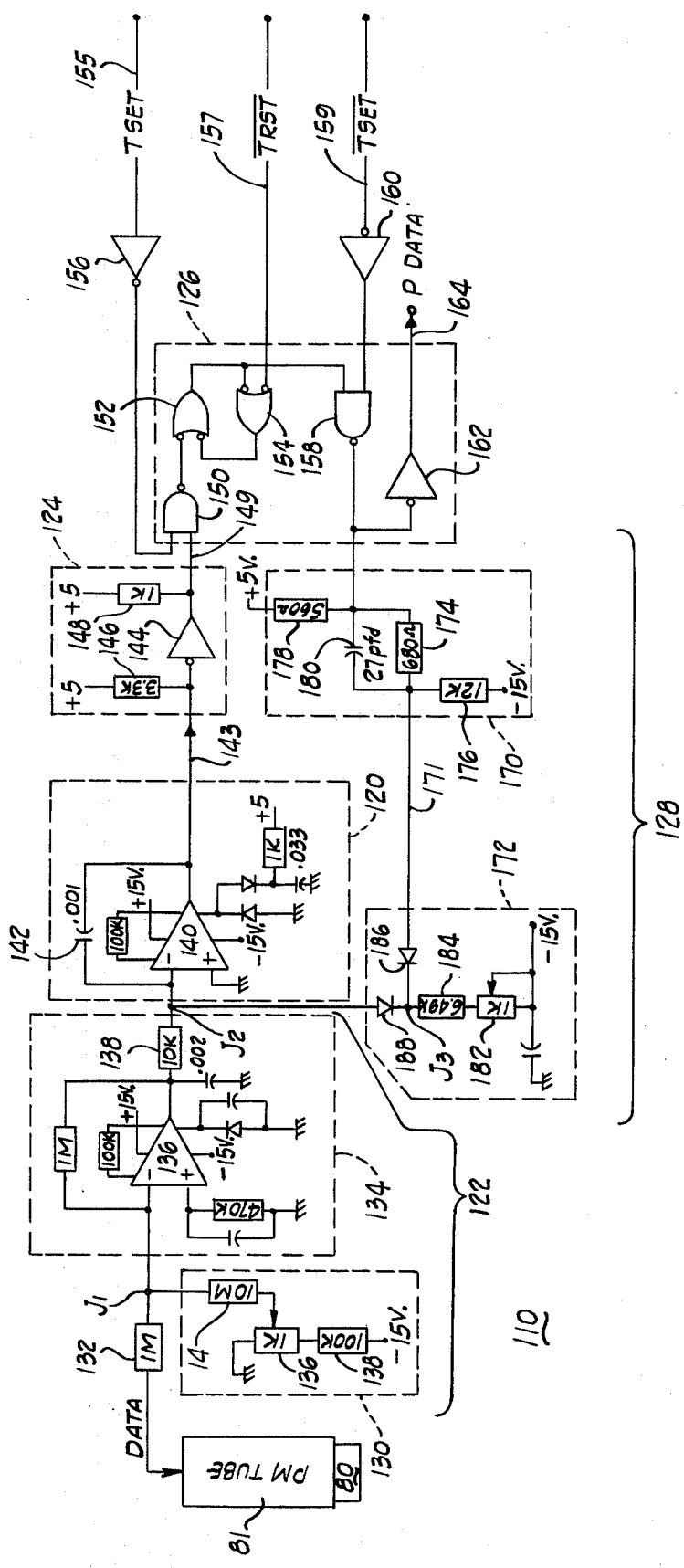
FIG. 5 is a circuit schematic of a pulse generator in the form of a charge pump integrator used in the scanning system of FIG. 1.

Referring now to FIG. 5 the pulse generator 110 includes an integrator 120 and a preamplifier stage 122 which amplifies current levels of the radiation signal for input to the integrator 120. The integrator 120 output is coupled to a threshold comparator 124 which generates an output whenever the integrator output exceeds the threshold of the comparator 124. An output circuit 126 receives the comparator output and is connected to a feedback circuit 128 coupled between the output circuit 126 and the input of the integrator 120. The feedback circuit dispenses an amount of charge to the integrator 120 for causing the integrator 120 to reset each time its output signal exceeds the threshold of the threshold comparator 124. Accordingly, the outputs of the integrator 120 and the comparator 124 are pulsating waveforms and the output circuit 126 produces PDATA pulses.

The preamplifier stage 122 includes a dark current adjusting circuit 130, a calibration resistor 132, and a current amplifier 134. The dark current adjusting circuit 130 adjusts the level of the radiation signal when no light is incident on the photomultiplier tube of the associated detector 94a. This current is known as the "dark" current and is preferably maintained at a predetermined low level so that the ratio of the maximum radiation signal current to the dark current is 1000:1. If the dark current should fall below the level necessary to maintain the 1000:1 ratio, the dark current adjusting circuit 130 automatically adds a restoring amount of current to the radiation signal. In the illustrated embodiment, the dark current compensation circuit maintains 10 nanoamps as the minimum current flowing out of the current amplifier 134.

The adjusting circuit 130 comprises a potentiometer 136 which is connected across a source of reference potential by a fixed resistor 138. The wiper of the potentiometer is connected to a junction J1 through a fixed resistor 140. The amount of dark current flowing out of the current amplifier 134 into the junction J1 is determined by adjustment of the potentiometer wiper position to control the voltage at the junction J1.

The current amplifier 134 includes a conventional operational amplifier 136 having its inverting input coupled to the junction J1 and its output connected to the integrator 120 via a resistor 138. The operational amplifier 136 is provided with bias circuitry for adjusting the output to the resistor 138 to be in the ratio of 1 volt output for each microamp input to the operational amplifier 136. The resistor 138 converts the voltage output from the operational amplifier 136 into a current output.

The integrator 120 is conventional and comprises an operational amplifier 140 having a feedback capacitor 142 coupling its output and its inverting input terminal. The inverting input terminal of the operational amplifier 140 is also connected to the resistor 138 at a junction J2 for receiving the amplified radiation signal and producing the integrator output on a line 143. The value of the capacitor 142 is selected according to the rate at which the output pulses from the comparator 124 will be generated. For a pulse repetition rate of the output pulses of one million PPS, the capacitor 142 is selected to have a .001 microfarad value.

The threshold comparator 124 includes a gate 144 having an input bias resistor 146 and an output bias resistor 148. The gate 144 has an approximate 1.5 volts threshold and, whenever the integrator output signal exceeds that threshold, the gate 144 produces an output on a line 149.

The output circuit 126 includes an input NAND gate 150, an RS flip-flop in the form of a pair of cross-coupled NAND gates 152, 154, and an output NAND gate 158. The input NAND gate 150 has one input coupled to the line 149 for receiving the output pulses and has another input coupled to a line 155 via an inverter 156 for receiving the TSET timing signal. The gate 154 has its noncross-coupled input coupled to a line 157 for receiving the $\overline{\text{TRST}}$ timing signal. The output gate 158 has one input coupled to the output of the gate 152 and has another input coupled to a line 159 via an inverter 160 for receiving the $\overline{\text{TSET}}$ timing signal. The output of the gate 158 is coupled to the feedback circuit 128 and to an inverter 162 for providing the PDATA pulses on a line 164.

Referring to FIGS. 9b and 9c, the trailing edge of the TRST timing signal is seen to be 100 nanoseconds before the rising edge of the TSET timing signal. This allows the RS flip-flop of gates 152, 154 to be reset to a logic one when the TSET timing signal goes to a logic zero and an output pulse is on the line 149. Because the $\overline{\text{TRST}}$ timing signal goes to a logic one state before TSET timing signal goes to a logic one state, the logic one is latched into the RS flip-flop so that a logic zero is transferred to the feedback circuit 128 when the $\overline{\text{TSET}}$ timing signal goes to a logic zero state (i.e., when the TSET timing signal goes to a logic one state).

Conversely the RS flip-flop is reset to a logic zero state in the absence of an output pulse on the line 149 when the $\overline{\text{TRST}}$ timing signal goes to a logic zero. This produces a logic one state to the feedback circuit 128.

The feedback circuit 128 comprises a noninverting level shifter circuit 170 connected to the output of the output NAND gate 158 and a charge supply circuit 172 connecting the output of the level shifter 170 to the input of the integrator 120 at the node J2.

The level shifter circuit 170 includes three serially connected voltage divider resistors 174, 176, 178 connected between positive and negative voltage supplies, and a capacitor 180 connected in parallel with the resistor 174. The input to the level shifter circuit 170 is the common connection of the resistors 174, 178, and the capacitor 180, and is connected to the output of the gate 158. The output of the level shifter circuit 170 is the common connection of the resistor 174, 176 and the capacitor 180. A logic one voltage at the output of the gate 158 causes the level shifter circuit 170 to generate a logic one output on a line 171 of approximately four volts. A logic zero produced at the output of the gate 158 generates a logic zero on the line 171 of approximately −0.8 volts.

The charge supply circuit 172 includes a potentiometer 182 which is resistively coupled to a junction J3 by a resistor 184, is capacitively coupled to circuit ground, and is coupled to a negative voltage supply. A diode 186 is connected to the line 171 and to the junction J3 and is poled such that a logic one signal on the line 171 forward biases the diode 186. A diode 188 couples the junctions J2, J3 and is poled for current flow from the junction J2 into the junction J3.

Operation of the feedback circuit 128 is fundamental to operation of the pulse generator 110 as a charge pump integrator. Assuming the initial conditions that the integrator 120 is intially discharged, then there is no output on the line 64, and the line 171 is a logic one which forward biases the diode 186 which in turn reverse biases the diode 188. Upon the detection of radiation by the associated radiation detection unit current flows from the current generator 134 through the junction J2 and into the integrator 120, charging the capacitor 142. As the capacitor 142 charges, the integrator output signal on the line 143 increases negatively in value until it falls below the threshold of the comparator 124. Upon this condition an output is generated on the line 149 which, upon generation of the TSET, $\overline{\text{TRST}}$, and $\overline{\text{TSET}}$ timing signals, produces an output on the line 164. This causes a logic zero to be generated on the line 171 which reverse biases the diode 186 and allows the diode 188 to become forward biased. Forward biasing of the diode 188 allows the capacitor 142 to rapidly discharge, increasing the value of the integrator output signal until it is above the threshold of the gate 144. This terminates the comparator output and results in completion of a PDATA pulse on the line 164. Upon completion of the PDATA pulse, the output circuit 126 and the level shifter circuit 170 cause a logic one to be generated on the line 171, forward biasing the diode 186. The voltage at the junction J3 increases, reverse biasing the diode 188 and allowing the capacitor 142 to be charged by the current from the current amplifier 134.

The illustrated charge pump amplifier is designed to draw approximately 2 milliamps of current out of the integrator 120. This is sufficient to allow the output pulses to be generated at a one-million-pulse-per-second rate when 10 microamps flow into the anode of the photomultiplier tube 81.

Figure 6:
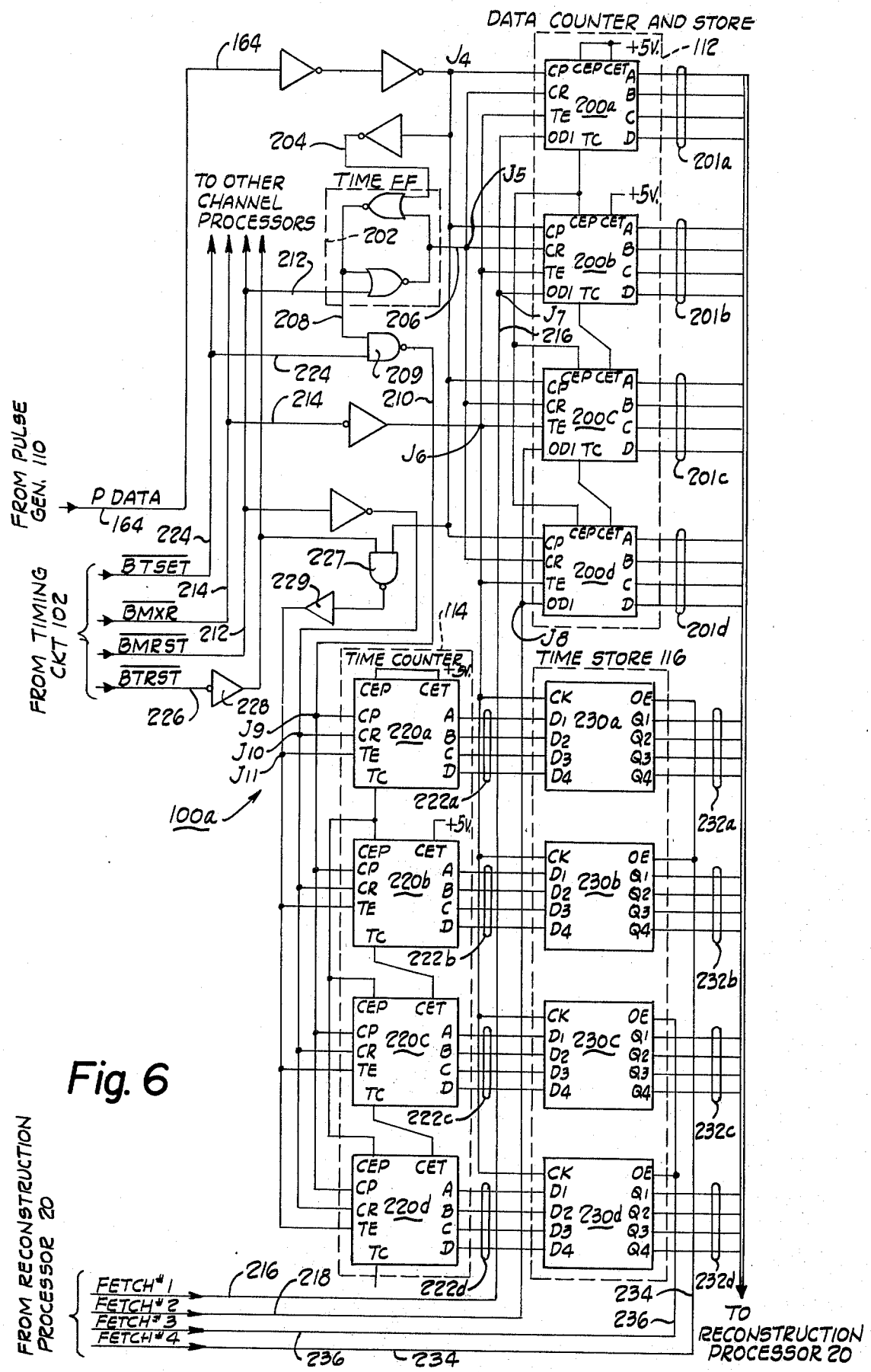
FIG. 6 is a schematic diagram of a time counter, a time store, and a data counter and store used in the scanning system of FIG. 1.

Referring now to FIG. 6 the data counter and store 112 includes a plurality of binary counter/output latch stages 200a-200d which are connected as a synchronous counter. Each of the counter/output latch stages is a model DM 8554 binary counter/latch which is commercially available from the National Semiconductor Corporation. Each stage has respective output lines 201a, 201b, 201c, 201d and produce four bits of the COUNT signal. Each stage has a clock pulse terminal CP connected to a junction J4 to which the PDATA pulses are coupled via the line 164 through a pair of inverters. Each of the stages 200a-200d also has counter reset terminals CR coupled to a junction J5 and has a transfer enable terminal TE coupled to a junction J6. Whenever a pulse is applied to the junction J5, the counter is reset, and whenever a pulse is applied to the junction J6, the count of each respective stage is transferred into its output latch. The junction J6 is coupled to a line 214 by an inverter for receiving the $\overline{\text{BMXFR}}$ signal for transferring the contents of the counter of each stage to the respective output latch immediately before each latch is cleared at the expiration of a primary time period.

Each stage also has a pair of count enable terminals CEP, CET, and a terminal count terminal, TC. The TC terminal of the stage 200a is coupled in parallel to the CEP terminals of the stages 200b, 200c, 200d. The TC terminals of the stages 200b, 200c are respectively coupled to the CET terminals of the stages 200c, 200d. Whenever the count enable terminals CEP, CET are coupled to logic one, occurrences of the PDATA pulses at the junction J4 increment the count of each stage. However, a logic one is generated at the terminal count terminal TC only when a logic 1111 state is produced in the respective counter so that synchronous counter operation is effected.

Each of the stages 200a-200d also has an output data enable terminal ODI, and the output data terminals of the stages 200a, 200b are coupled to a junction J7 and the output data terminals of the stages 200c, 200d are connected to a junction J8. Whenever FETCH 1, FETCH 2 pulses are received at the junctions J7, J8, from the reconstruction processor 20, the latch count in the respective stages is transferred onto the lines 200a-200d for transmission to the reconstruction processor 20.

A time flip-flop 202 has one input coupled by a line 204 through an inverter to the junction J4 and has another input coupled by a line 212 to receive the $\overline{\text{BMRST}}$ timing signal. It has one output coupled to the junction J5 via a line 206 and has another output coupled to a gate 209 by a line 208. When the BMRST timing signal goes to a logic zero state on the line 212, representing the end of a primary time period, the time flip-flop 202 is reset. This produces a logic one at the junction J5, which in turn resets all the stages 200a-200d. Upon the next occurrence of one of the PDATA pulses at the junction J4 after the beginning of a subsequent primary time period, the time flip-flop 202 is set via the line 204, producing a logic zero at the junction J5. This produces a logic one on the line 208 and enables the gate 209. The gate 209 has another input coupled to a line 224 for receiving the BTSET timing signal, so that the logic one on the line 208 allows the gate 209 to produce a clock signal on a line 210 according to occurrences of the BTSET timing signals. This is transferred by the line 210 to a junction J9 for use by the time counter 114.

The time counter 114 includes a plurality of binary counter/output latch stages 220a-220d. Each of these stages 220a-220d have terminals respectively identical to the stages 200a-200d and are interconnected in synchronous counter fashion. The node J9 corresponds to the node J4, a node J10 corresponds to the node J5 and a node J11 corresponds to the node J6 for operating the respective stages 220a-220d as a synchronous counter. However, contrary to the connection of the stages 200a-200d, the output data terminals ODI of the stages 220a-220d are conditioned such that the contents of the output latches are automatically introduced onto the respective sets of output lines 222a-222d.

More specifically, the clock signals from the gate 209 are coupled to the junction J9 for incrementing the stages 220a-220d whenever the time flip-flop 202 is set by the occurrence of the first PDATA pulse occurring during a primary time period. The contents of the stages 220a-220d is transferred to the respective output latches as the time signal upon the occurrence of each PDATA pulse immediately after the incrementing of each stage. To this end, a gate 227 receives on one input the $\overline{\text{BTRST}}$ signal on the line 226 via an inverter 228 and receives the PDATA pulses from the junction J4 on its other input. Upon coincidence of a logic zero state of the $\overline{\text{BTRST}}$ signal and a PDATA pulse, the gate 227 generates a logic one via an inverter 229 to the junction J11. This transfers the contents of the respective counters to the respective output latches of the stages 220a-220d each time the counter 114 is incremented.

The stages 220a-220d are reset concurrently with the stages 200a-200d at the end of each primary time period.

Each logic zero state of the $\overline{\text{BMRST}}$ signal causes logic ones to be coupled to the junctions J5, J10, which resets the stages.

The time store 116 is also shown in FIG. 6 and comprises a plurality of four bit registers 230a-230d. Each of the registers 230a-230d has its input terminals coupled to the respective lines 222a-222d from the associated stages 220a-220d. A clock terminal CK on each of the registers 230a-230d is commonly connected to the junction J6 to allow the stages 230a-230d to receive and store the time signal on the lines 222a-222d upon generation of the $\overline{\text{BMXFR}}$ signal at the expiration of each primary time period. The stored time signal is output onto respective output lines 232a-232d whenever a respective output enable OE terminal is pulsed. To this end, a line 234 is connected to the output enable terminals OE of the sections 230a-230b and a line 236 is coupled to the output enable OE terminals of the sections 230c-230d. The lines 234, 236 are sequentially pulsed by FETCH 3, FETCH 4 signals from the reconstruction processor 20 for retrieving the stored data time in sequential bytes, with each byte consisting of eight bits.

Figure 7:
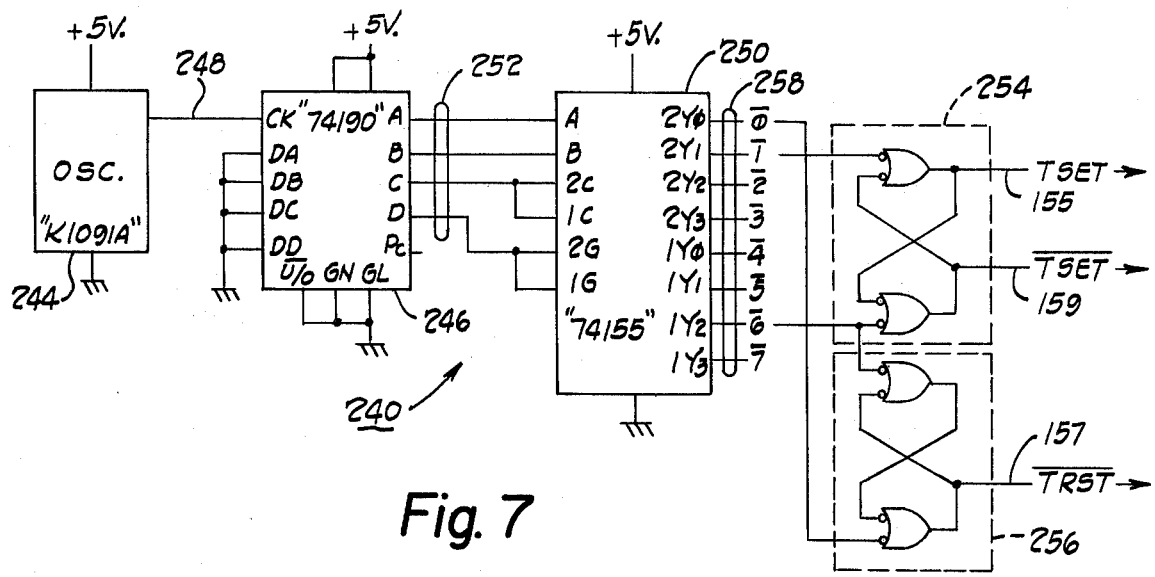
FIGS. 7 and 8 are schematic diagrams of timing generators used in the scanning system of FIG. 1.
Figure 8:
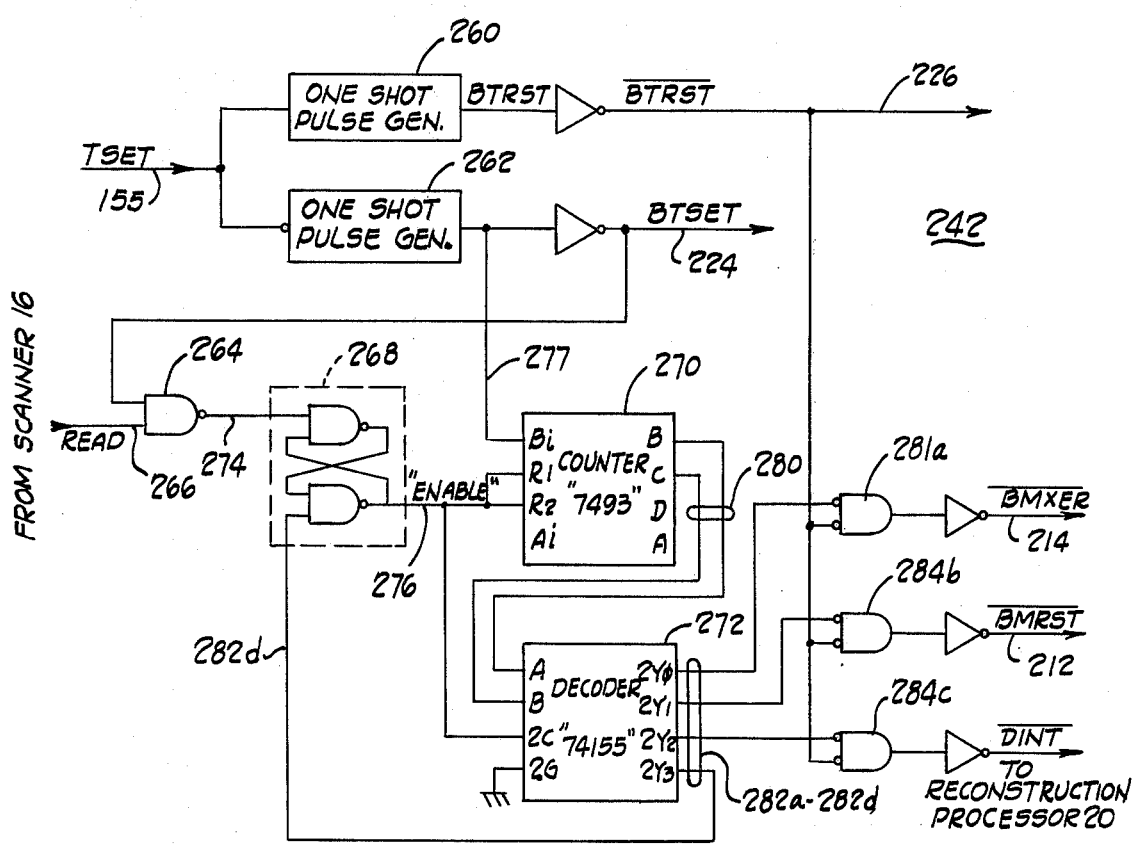

The timing circuit 102 includes a nonbuffered signal generator 240 which is shown in FIG. 7 and a buffered signal generator 242 which is shown in FIG. 8. The nonbuffered signal generator 240 generates the TSET, $\overline{\text{TSET}}$, and $\overline{\text{TRST}}$ timing signals on the lines 155, 159, 157 respectively. The buffered signal generator 242 is responsive to the TSET timing signal on the line 155 and to the index signal from the scanner 16 for producing the $\overline{\text{BTRST}}$, $\overline{\text{BTSET}}$, $\overline{\text{BMXFR}}$, and $\overline{\text{BMRST}}$ timing signals on the lines 226, 224, 214, and 212 respectively.

Referring to FIG. 7, the nonbuffered signal generator 240 includes an oscillator 244, a counter 246 coupled to the oscillator 244 via a line 248, a decoder 250 coupled to the counter 246 via a set of lines 252, and a pair of latch circuits 254, 256 connected to outputs of the decoder 250. The oscillator 244 is a 10 megahertz crystal oscillator which is commercially available from Motorola, Inc., under the designation K1091A. The oscillator generates a ten-megahertz waveform on the line 248 for periodically incrementing the counter 246. FIG. 9a illustrates the ten-megahertz waveform.

The counter 246 is any suitable decade counter such as a model 74190 from Texas Instruments, Inc. The counter 246 generates signals on the lines 252 representative of the binary state of the counter 246 as it periodically counts between zero and nine.

The decoder 250 is a dual 1:4 decoder which is operatable as a 2:8 decoder. One such decoder is commercially available from Texas Instruments, Inc. as Model No. 74155. The decoder 250 has its input terminal coupled to the lines 252 and has a set of output lines 258 coupled to the latch circuits 254, 256. As the counter 246 counts between 0 and 9, the decoder 250 sequentially energizes ones of the lines 258 every 100 nanoseconds, with a period of 300 nanoseconds lapsing between the 111 output state and the subsequent 000 output state.

The latch circuit 254 is coupled to the decoder 250 via the lines 258 representing the 001 and the 110 decoded states for generating the TSET and the $\overline{\text{TSET}}$ output signals respectively on the lines 155, 159. The latch circuit 254 is set via the occurrence of the 001 state to produce the TSET signal and is reset by the occurrence of the 110 state to produce the $\overline{\text{TSET}}$ signal.

The latch circuit 256 is coupled to the decoder 250 via the lines 258 to produce the $\overline{\text{TRST}}$ signal on the line 157. The latch circuit 256 is set by the occurrence of the 110 state and is reset via the occurrence of the 000 state to produce the $\overline{\text{TRST}}$ signal.

Waveforms 9a–9c in FIG. 9 illustrates generation of the TSET and TRST signal. FIG. 9a depicts the output of the oscillator 244 as a ten-megahertz square wave. The TSET signal is shown in FIG. 9b as a logic one during the first through fifth pulses of each ten-pulse cycle, and is a logic zero during the six through tenth pulses of each ten-pulse cycle. FIG. 9c shows the TRST signal as a logic zero during the tenth through fifth pulses of each ten-pulse cycle and is a logic one during the sixth through ninth pulse of each ten-pulse cycle. As shown by a comparison of FIGS. 9b, 9c, there is a 100 nanosecond duration which the TSET and TRST signal are both logic zeros. This allows the RS flip-flop configuration of the gates 152, 154 to properly latch upon the occurrence of one of the output pulses on the line 149.

Referring now to FIG. 8, the buffered signal generator 242 includes a pair of one-shot pulse generators 260, 262 responsive to the TSET signal on the line 155 for respectively generating the $\overline{\text{BTRST}}$ timing signal and the BTSET timing signal on the lines 226, 224 respectively. The $\overline{\text{BTRST}}$ and BTSET timing signals are effectively two-phase clock signals operating at a one-megahertz frequency and having a 25% duty cycle. FIGS. 9d and 9e show the BTRST and the BTSET signals as being relatively phase displaced by 250 nanoseconds.

The one-shot pulse generators 260, 262 are commercially available from Texas Instruments, Inc. as a model 74221 dual one-shot generator having one generator triggered by positive-going pulses and one generator triggered by negative-going pulses. Each pulse generator is voltage biased to produce the $\overline{\text{BTRST}}$ signal as a 250-nanosecond pulse upon the leading edge of each TSET pulse, and to produce the BTSET signal as a 250-nanosecond pulse upon the trailing edge of each TSET pulse.

The buffered signal generator 242 also includes a master buffer section which is coupled to the scanner 16 for producing the $\overline{\text{BMXFR}}$ and the $\overline{\text{BMRST}}$ signals to be indicative of the end of each primary time period during which the average intensity signal is to be calculated.

The master buffer section includes a gate 264 which is responsive to the BTSET timing signal and to the index signal on a line 266 from the scanner 10. A latch 268 is coupled to the gate 264 by a line 274 and generates an ENABLE signal on a line 276 upon the occurrence of the BTSET signal and the index signal.

A counter 270 and a decoder 272 are coupled to the line 276. A line 277 connects the one-shot pulse generator 262 to the counter 270 so that, upon generation of the ENABLE signal on the line 276, the counter 270 is incremented through four states upon four occurrences of the BTSET timing signal. The decoder 272 is coupled to the counter 270 via a pair of lines 280 for energizing one of its output lines 282a–282d for each of the four states of the counter 270. A gate 284a is coupled to the line 282a and to the line 226 for producing the BMXFR signal which is inverted and supplied on the line 214.

A gate 284b is coupled to the line 282b and to the line 226 for producing the BMRST signal on the second count of the counter 270. The BMRST signal is inverted and supplied to the line 212.

A gate 284c is coupled to the line 282c and to the line 226 for producing a data interrupt, DINT, signal which is coupled to the reconstruction processor 20. The $\overline{\text{DINT}}$ signal is indicative that the data accumulated in the signal processor 94 is ready to be transferred to the reconstruction processor 96. The DINT signal is generated via the third count of the counter 270.

The latch 268 has an input coupled via the line 282d to the decoder 262 for being reset upon the fourth count of the counter 270. This removes the ENABLE signal from the line 276 and clears the counter 270, awaiting the expiration of the next primary time period.

The index, $\overline{\text{MBXFR}}$, $\overline{\text{BMRST}}$, and $\overline{\text{DINT}}$ signals are shown in FIGS. 9f–9i. The index signal is generated by the scanner 10 as a pulse of approximately two-microseconds duration at the end of each primary time period. The occurrence of the first BTSET signal causes the $\overline{\text{BMXFR}}$ signal to be generated on the line 214 which, in turn, causes transfer of the TIME signals into the time store 116 and causes the COUNT signals to be latched into the output latch of the stage 200a–200d. The occurrence of the second BTSET signal causes the $\overline{\text{BMRST}}$ signal to be generated on a line 212, causing reset of the time counter 114 and of the stages 200a–200d. The occurrence of the third BTSET signal causes generation of the $\overline{\text{DINT}}$ signal, and the occurrence of the fourth BTSET signal resets the latch 268.

It is thus apparent that an improved radiation measuring and processing unit has been provided for a radiation scanning system. The average intensity of the beam of radiation as it impinges upon the radiation detector during a primary time period is accurately determined by computing the average rate of a train of intensity representing pulses occurring during a secondary time period whose duration is determined according to the occurrences of the pulses within the primary time period. This allows the duration of the secondary period to be accurately determined. Since the number of pulses occurring within a secondary period can be accurately determined, the number of the intensity representing pulses can be precisely averaged to give an indication of the average intensity of the beam impinging upon the detector. The radiation scanning system also features a novel charge pump integrator. The charge pump integrator accurately generates the intensity representing pulses with an extraordinarily high degree of efficiency and without complicated and expensive electronics.

Although the invention has been described in its preferred form with a certain degree of particularity, it is understood that the present disclosure of the preferred form has been made only by way of example. Numerous changes in the details of the measuring and processing unit, as well as applications other than with a tomographic scanning system, may be resorted to without departing from the spirit and the scope of the invention as claimed.

What is claimed is:

1. An X-ray scanning system comprising:
   a. an X-ray source for producing a beam of X-rays;
   b. beam receiving means disposed for receiving the X-ray beam and producing a train of pulses whose instantaneous repetition rate is indicative of the instantaneous intensity of the beams as it emerges from the object and inpinges upon an receiving means;
   c. means supporting at least one of said X-ray source and beam receiving means for motion along a predetermined path relative to the object with said beam being scanned through said object during said motion;

d. timer means for generating a time signal having a value representative of the time elapsing between selected pulses of said pulse train which occur during a predetermined interval of said scanning motion;

e. a counter for counting pulses of the pulse train occurring within said time interval and producing a count signal; and, f. means for comparing the count signal with the time signal for generating an average intensity signal indicative of the average intensity of said X-ray beam impinging on said beam receiving means in said interval.

2. The scanning system according to claim 1 and further including time stores and data stores for storing the values of said time signal and said count signal after each of a sequence of said predetermined intervals, and said comparator means is responsive to said stored time signal and to said stored count signal to produce said average intensity signal.

3. The X-ray scanning system according to claim 1 wherein the beam receiving means includes a scintillator crystal and a photomultiplier tube.

4. The X-ray scanning system according to claim 1 wherein the beam receiving means comprises an X-ray responsive means for producing an analog data signal having a value indicative of the intensity of X-rays impinging on said responsive means and a charge-pulse integrator having:

a. an integrator responsive to the analog data signal for producing an integrator output signal and having a feedback capacitor coupling its input and its output;

b. a threshold level detector coupled to the output of the integrator, said level detector rendered effective to produce a detector output whenever the integrator output signal exceeds the threshold of the threshold level detector; and, c. feedback means coupled to the integrator input and responsive to the detector output for selectively discharging the feedback capacitor by a selected amount each time a detector output is sensed and thereby producing one of said data pulses at the detector output.

5. The X-ray scanning system according to claim 4 wherein the X-ray source includes means for generating a plurality of said beams, said X-ray responsive means includes a plurality of scintillation crystal and photomultiplier tube assemblies for generating a like plurality of said analog signals, respectively, for transmission to a like plurality of said charge-pulse integrators for producing a plurality of said pulse trains, and a like plurality of said timer means for producing time signals associated with each pulse train.

6. A tomographic scanning system comprising:

a. a source of penetrative radiation for producing a beam of radiation;

b. source supporting means for moving said source along a predetermined path relative to a subject being scanned;

c. beam receiving means comprising a detector disposed for receiving the beam of radiation emerging from the subject during said scanning motion, said beam receiving means producing a train of data pulses whose instantaneous frequency is indicative of the intensity of the radiation impinging on said detector;

d. period defining means for establishing a primary time period during which a predetermined amount of scanning motion occurs;

e. timing means for producing a time signal representing a time interval between selected pulses occurring within said primary time period, said time interval having a duration less than said primary time period;

f. count signal producing means for producing a count signal related to the number of pulses occurring during said primary time period; and, g. comparator means for comparing said count signal and said time signal and producing an output signal indicative of the average radiation intensity detected during the primary time period.

7. The tomographic scanning system according to claim 6 wherein the beam receiving means includes:

a. a scintillator crystal for producing an analog data signal; and, b. converter means for converting the analog data signal into said train of data pulses.

8. The scanning system according to claim 6 wherein the timing means comprises:

a. a timer actuated by the first data pulse occurring during said primary time period for producing timing signals having values which represent the time elapsed after said first data pulse; and, b. storage means for producing said time signal, said storage means effective to store the instantaneous timing signal value from said timer at the occurrence of each data pulse during said interval subsequent to said first data pulse whereby the timing signal value store at the occurrence of the last data pulse in the interval is the time signal.

9. The scanning system according to claim 8 further including a first counter incremented by the second and each subsequent data pulses in the train occurring during the primary time period, said timer comprising a second counter for coupling the timing signals to the storage means whenever the first counter is incremented.

10. A method of determining the intensity of radiation detected during a tomographic examination comprising:

a. producing a beam of penetrative radiation from a radiation source and directing the beam through a subject for examination;

b. detecting radiation emerging from the subject;

c. scanning the beam through the subject via a predetermined scan path by effecting relative motion between the subject and the radiation beam;

d. producing a train of signal pulses having an instantaneous frequency corresponding to the instantaneous intensity of the radiation emerging from the subject;

e. detecting individual pulses occurring during a predetermined segment of the scan path and producing a count signal having a value related to the number of pulses detected;

f. timing the interval between pulses occurring during the scan segment and producing a corresponding time signal;

g. comparing the count and time signals; and h. producing an average intensity signal having a value representing the average intensity of radiation emerging from the subject during the scan segment.

11. The method claimed in claim 10 wherein producing a train of signal pulses comprises producing analog signals having levels proportional to the intensity of radiation impinging on a radiation detector and converting said analog signals to said pulse train with the pulse train frequency varying in relation to variations of said analog signal level.

12. The method claimed in claim 10 further including producing signals indicating the beginning and ending of each scan path segment of a succession of scan path segments, producing said count and time signals after production of each signal indicating the beginning of a scan path segment and prior to each signal indicating the end of the scan path segment.

13. A tomographic scanning system for producing an image of a cross section of a subject in response to radiation emerging from the subject comprising:
  a. radiation detector means including at least a detector supported for movement along a path for receiving radiation emerging from the subject, said detector means producing a train of output pulses having an instantaneous frequency corresponding to the instantaneous intensity of the radiation as it impinges upon the detector;
  b. position indicating means for generating index signals indicative of the traversal by said detector through each of a series of segments constituting said path, and
  c. a signal processing unit responsive to said pulse train and to said index signals for generating an average intensity signal over a primary time period corresponding to the traversal of said radiation detector through one of the segments, the processing unit including:
  i. pulse responsive means for producing an output signal having a value depending upon the number of pulses occurring during each path segment;
  ii. timer means for producing an output signal having a value determined by the time elapsing between the occurrences of pulses produced during each path segment; and,
  iii. comparator means for comparing the output signals produced during respective scan segments and producing an average intensity signal representing the average intensity of radiation impinging on said detector during said respective scan segments.

14. The tomographic scanning system according to claim 13 further including drive means for moving the radiation detector means along said path to provide traversal of said segments respectively at substantially equal rates.

15. The tomographic scanning system according to claim 13 including support structure coupled to said radiation detector means for constraining movement of said radiation detector means to an orbital path.

16. The tomographic scanning system according to claim 15 further including drive means for moving the radiation detector means along said orbital path to provide said traversal through the segments at substantially equal rates.

17. The tomographic scanning system according to claim 13 wherein the position indicating means includes an encoder mechanism for generating pulses forming said index signals.

18. The scanning system claimed in claim 6 wherein said source of penetrative radiation is defined by an X-ray source, said detector comprises signal producing means for producing an analog signal which varies in accordance with variations in intensity of radiation impinging on said detector and said beam receiving means comprises a charge-pump integrator circuit for producing said pulse train in response to said analog signal, said charge pump integrator comprising:
  i. an integrator having an input and an output coupled together by a capacitor, said integrator responsive to said analog signal and producing an integrated data signal at its output;
  ii. a threshold level detector having its input connected to the integrator output, said threshold level detector producing an output signal in response to integrated data signal levels exceeding a predetermined threshold value; and
  iii. feedback means coupling the level detector output to the integrator input, said feedback means discharging said capacitor by a predetermined amount in response to production of a level detector output signal whereby the integrator output signal value is reduced below said threshold and an output pulse from the level detector is produced, said output pulse forming one pulse of said train.

* * * * *